United States Patent
Patel et al.

(10) Patent No.: US 8,589,424 B1
(45) Date of Patent: Nov. 19, 2013

(54) METHOD AND SYSTEM FOR ACCURATE MEDICAL-CODE TRANSLATION

(75) Inventors: Parag Patel, Bellevue, WA (US);
Abhishek Jacob, Bellevue, WA (US);
Virendra Prasad, Bellevue, WA (US);
Vijay Bhuttar, Bellevue, WA (US);
Ryan McDermitt, Bellevue, WA (US)

(73) Assignee: Edifecs, Inc., Bellevue, WA (US)

( * ) Notice: Subject to any disclaimer, the term of this patent is extended or adjusted under 35 U.S.C. 154(b) by 0 days.

(21) Appl. No.: 13/472,767

(22) Filed: May 16, 2012

(51) Int. Cl.
*G06F 17/30* (2006.01)

(52) U.S. Cl.
USPC .......................................... 707/756; 707/758

(58) Field of Classification Search
USPC ......................................... 707/602, 756, 758
See application file for complete search history.

(56) References Cited

U.S. PATENT DOCUMENTS

| | | | |
|---|---|---|---|
| 2008/0040150 A1* | 2/2008 | Kao | 705/2 |
| 2009/0112882 A1* | 4/2009 | Maresh et al. | 707/10 |
| 2011/0040576 A1* | 2/2011 | Madan et al. | 705/3 |

* cited by examiner

*Primary Examiner* — Thu-Nguyet Le
(74) *Attorney, Agent, or Firm* — Olympic Patent Works PLLC

(57) ABSTRACT

The current application is directed to methods and systems for translation of medical codes, including translation of codewords from one medical-concept code to another. The method and systems to which the current application is directed employ a multi-step translation process to translate a source codeword to a corresponding target codeword, associating the source codeword with underlying medical concepts which are, in turn, used to identify candidate target codewords of another medical-concept code. A variety of different weighting-based and filter-like criteria are then employed to select a target codeword from the candidate target codeword. The methods and systems to which the current application is directed provide for more accurate and reliable translations than would be obtained using naive, simple table-based translation.

24 Claims, 11 Drawing Sheets

METHOD AND SYSTEM FOR ACCURATE MEDICAL-CODE TRANSLATION

TECHNICAL FIELD

The current application is directed to translation of medical codes and, in particular, to a method and system for accurately transmitting medical codewords from one medical-concept code to another, different, medical-concept code.

BACKGROUND

Many different medical-concept codes have been developed, including various versions of the International Statistical Classification of Diseases and Related Health Problems ("ICD"), including ICD-9 and ICD-10, as well as the systematized nomenclature of medicine ("SNOMED"). These different types of medical-concept codes provide hierarchical, alpha-numeric medical codewords for each of many different types of pathologies, diagnostics, treatments, and other medically related concepts, generally along with textural annotations and other information, much like books in libraries are encoded using the Dewey Decimal System. Medical codes are widely employed in healthcare-billing services, electronic medical records ("EMRs"), and other types of medically related information that is digitally encoded in electronic, electromagnetic, and electro-optical mass-storage devices and memories, accessed by a variety of different types of electronic data-processing systems, and displayed on various types of electronic display devices. Unfortunately, the different medical-concept codes use different alpha-numeric encodings for codewords, have different hierarchical organizations, and contain codewords that correspond to different sets of underlying concepts. It is often necessary, when processing EMRs, healthcare-billing paperwork, and other medically related information, to translate codewords from one medical-concept code to another. For example, a healthcare clinic may internally use codewords from a first medical-concept code and may need to translate these codewords to corresponding codewords of a second medical-concept code used by an insurance provider in order to facilitate processing of invoices submitted by the healthcare clinic to the insurance provider. In another example, organizations may migrate from one medical-concept code to another, the migration process involving translation of codewords stored in current EMRs and invoices to corresponding codewords of a different medical-concept code to avoid using two different types of electronic medical-data processing systems.

Unfortunately, medical-concept codes are enormous, containing many thousands of different codewords, each potentially related to numerous different underlying medical concepts. Manual translation of medical codes would be far too time-consuming and error-prone to be practical for even low-volume translation of codewords from a first medical-concept code to a second, related medical-concept code. In many cases, erroneous translation can lead to delays, unnecessary costs, and other serious and even life-threatening consequences. Because the codewords of one medical-concept code often do not conceptually align with the codewords of another medical-concept code, medical-code translation is, by nature, inexact and far from straightforward. For these reasons, medical providers, insurance companies, EMR processing companies, and many other organizations involved in medically related fields seek accurate and efficient medical-code translation to facilitate various different types of medically related tasks and operations.

SUMMARY

The current application is directed to methods and systems for translation of medical codes, including translation of codewords from one medical-concept code to another. The method and systems to which the current application is directed employ a multi-step translation process to translate a source codeword to a corresponding target codeword, associating the source codeword with underlying medical concepts which are, in turn, used to identify candidate target codewords of another medical-concept code. A variety of different weighting-based and filter-like criteria are then employed to select a target codeword from the candidate target codeword. The methods and systems to which the current application is directed provide for more accurate and reliable translations than would be obtained using naive, simple table-based translation.

DETAILED DESCRIPTION

The current application is directed to methods and systems for automated translation of medical codes. These methods and systems employ multi-step automated translation in which a source codeword is associated with underlying medical concepts. Candidate target codewords are then identified using the associations of the source codeword with underlying medical concepts as well as associations of the candidate target codewords with the same underlying medical concepts. A target codewords is selected from among the candidate target codewords using weighted-association comparisons, filters, and other methods.

Figure 1:
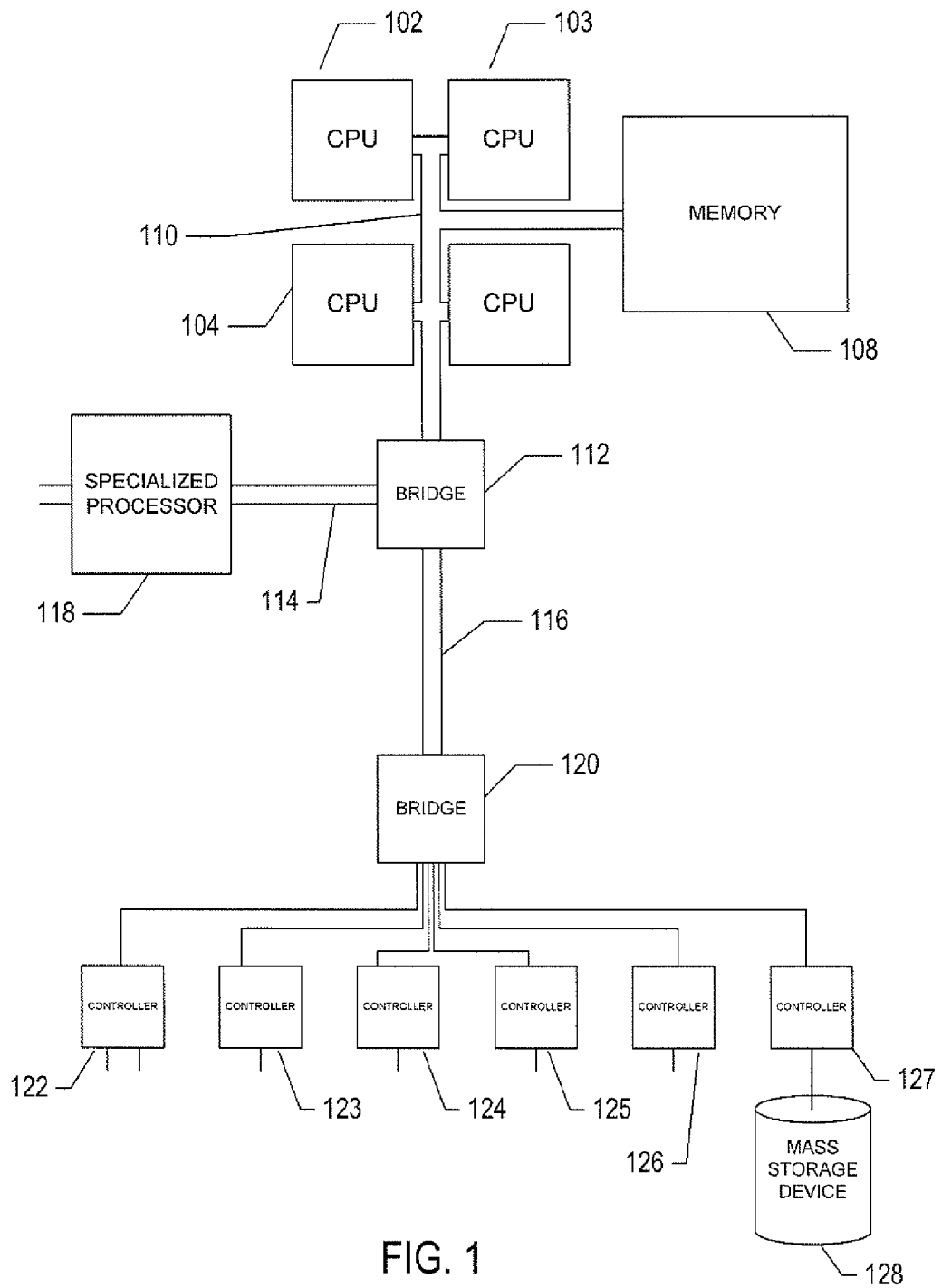
FIG. 1 illustrates a block diagram of an example computer system that, when controlled by appropriate computer instructions, implements certain of the medical-code translation systems to which the current application is directed and electronically carries out certain of the medical-code translation methods to which the current application is directed.

It should be emphasized, at the onset, that the currently described methods and systems carry out real-world, important, useful tasks that result in physical transformations of electronic, electromagnetic, and electro-optical data-storage devices, electronic display of encoded information, and physical computational activities that provide tangible, real-world results. While the systems to which the current application is directed are complex computational and data-processing systems controlled by many different levels of computer instructions, these are real, tangible, physical systems that carry out real-world tasks. FIG. 1 illustrates a block diagram of an example computer system that, when controlled by appropriate computer instructions, implements certain of the medical-code translation systems to which the current application is directed and electronically carries out certain of the medical-code translation methods to which the current application is directed. The computer system contains one or multiple central processing units ("CPUs") 102-105, one or more electronic memories 108 interconnected with the CPUs by a CPU/memory-subsystem bus 110 or multiple busses, a first bridge 112 that interconnects the CPU/memory-subsystem bus 110 with additional busses 114 and 116, or other types of high-speed interconnection media, including multiple, high-speed serial interconnects. These busses or serial interconnections, in turn, connect the CPUs and memory with specialized processors, such as a graphics processor 118, and with one or more additional bridges 120, which are interconnected with high-speed serial links or with multiple controllers 122-127, such as controller 127, that provide access to various different types of mass-storage devices 128, electronic displays, input devices, and other such components, subcomponents, and computational resources.

Figure 2A:
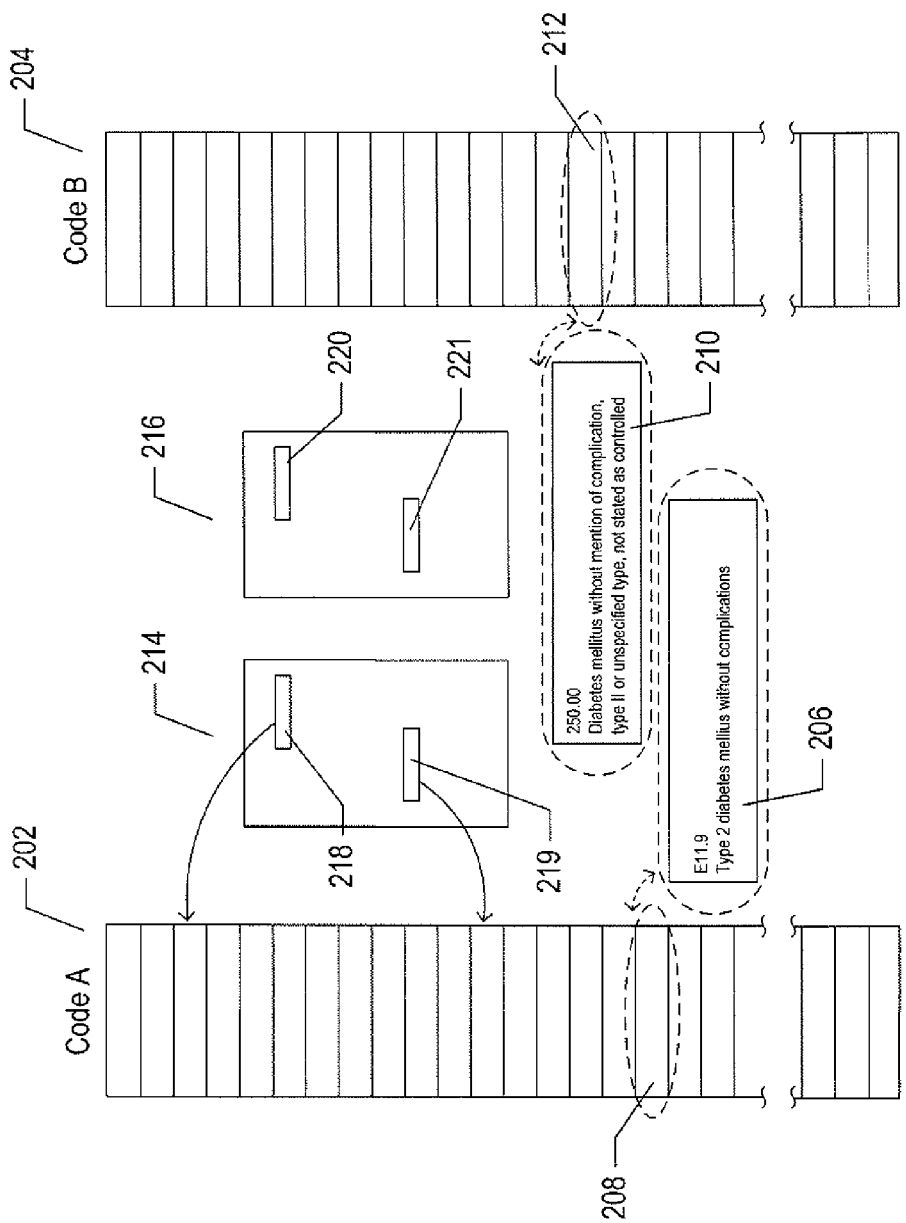
FIGS. 2A-B illustrate typical medical-code-translation tasks addressed by example methods and systems to which the current application is directed.
Figure 2B:
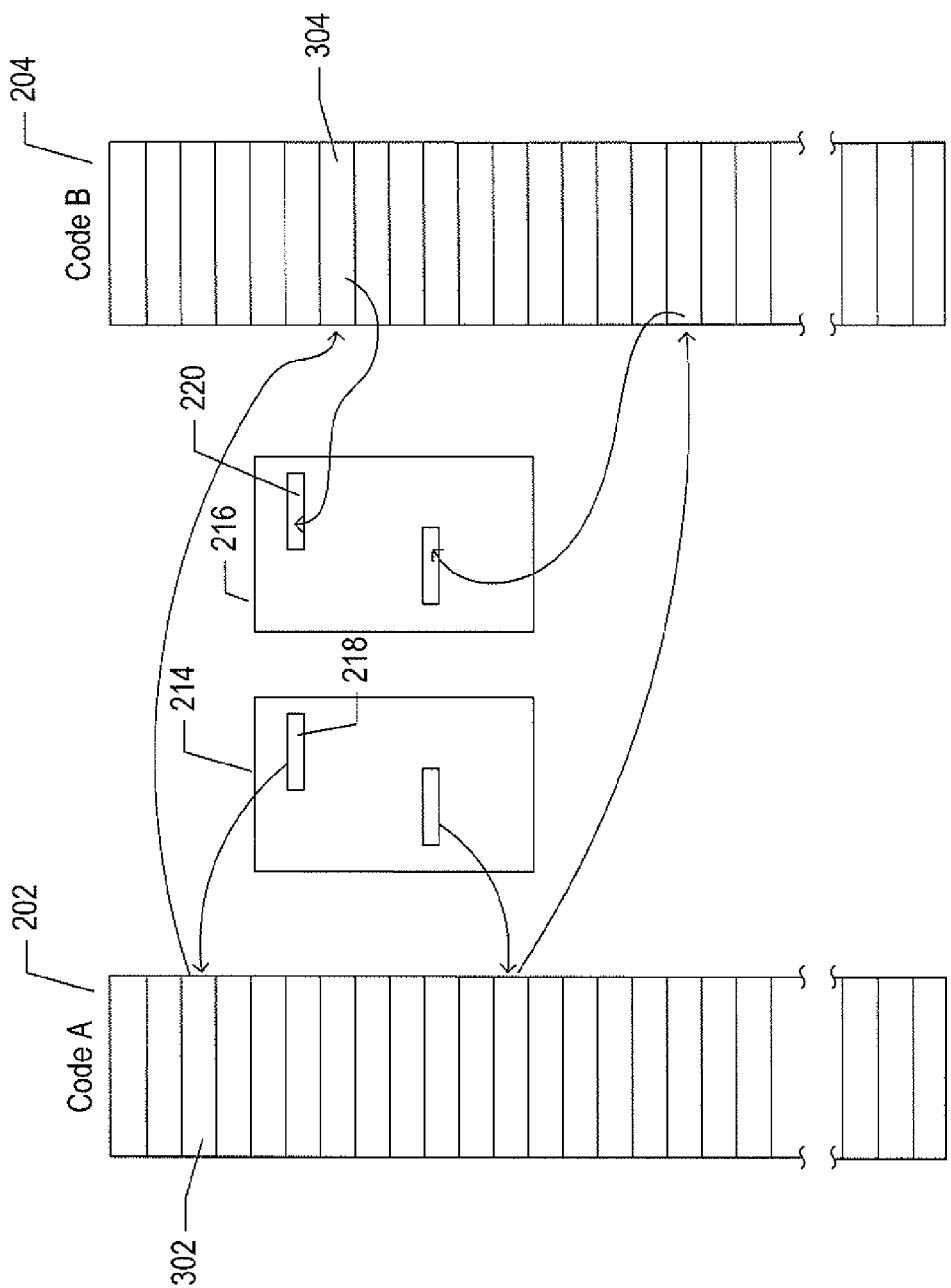

FIGS. 2A-B illustrate typical medical-code-translation tasks addressed by example methods and systems to which the current application is directed. In FIG. 2A, a first column of entries 202 represents a first medical-concept code and the second column of entries 204 represents a second medical-concept code. Partial representative contents for two entries, one entry from each column, are also shown in FIG. 2A. The partial contents 206 for entry 208 of column 202 and the partial contents 210 for entry 212 of column 204 illustrate two different, but related codewords, a first codeword selected from the ICD-9 medical-concept code and a second codeword selected from the ICD-10 medical-concept code. Two EMRs 214 and 216 are also shown in FIG. 2A. The first EMR includes codewords 218-219 of medical-concept code 202. It is desired to produce a copy EMR 216 identical to EMR 214, but with different medical codewords 220-221 from the second medical-concept code 204 corresponding to medical codewords 218 and 219 in EMR 214.

FIG. 2B illustrates a naive, although desirable, automated translation process. FIG. 2B uses the same illustration conventions as FIG. 2A. To produce the copy EMR 216 with translated codewords, for each codeword in the original EMR 214, such as codeword 218, the automated translator might look up the codeword in the first medical-concept code to find an entry 302 corresponding to the codeword, then either follow a reference in that entry to a corresponding entry 304 in the target code or use a separate translation table in which codewords from the first, source code 202 are paired with their equivalent codewords from the second medical-concept code 204, to obtain a reference to the appropriate target-code entry 304, and then use the target codeword and, in certain cases, other information from entry 304 to insert a codeword translation 220 into the target EMR 216. In the simplest case, the codeword translation would be a substitution of one alpha-numeric value for another alpha-numeric value, such as the value "250.00" for the codeword "E11.9," using the example in FIG. 2A. In other cases, information that annotates the codewords may be used in addition to, or instead of, codewords in the translation process. In still additional cases, multiple, related target codewords may be used to replace a single source codeword. Unfortunately, because the source and target medical-concept codes are generally differently organized, and each contains codewords that do not exactly correspond to, or match, codewords in the other medical-concept code, a simple translation process such as that shown in FIG. 2B is generally not possible or, if attempted, would result in translation with poor accuracy.

An approach used in systems and methods for medical-code translation to which the current application is directed is next provided, using graphical illustrations, an example implementation using the structured query language ("SQL") and relational databases, pseudocode, and control-flow diagrams. It should be emphasized, initially, that this discussion is not intended to cover all possible implementations or provide minute details of a particular approach within the overall approach provided below as an example. Instead, the discussion is intended to expose principles and concepts underlying many different possible implementations of the systems and methods for medical-code translation to which the current application is directed and using which particular implementations can be designed and produced.

A first step that facilitates the currently described medical-code translation process is to generate a medical-concept database. In general, generation of the medical-concept database may be carried out by using either manual, human-analyst-based methods or by using automated methods that employ natural-language processing, detailed translation rules, and inference engines. Perhaps the most productive approach is to combine both automated, semi-automated, and manual approaches to ensure that a robust, well-designed, and complete medical-concept database is prepared.

Figure 3:
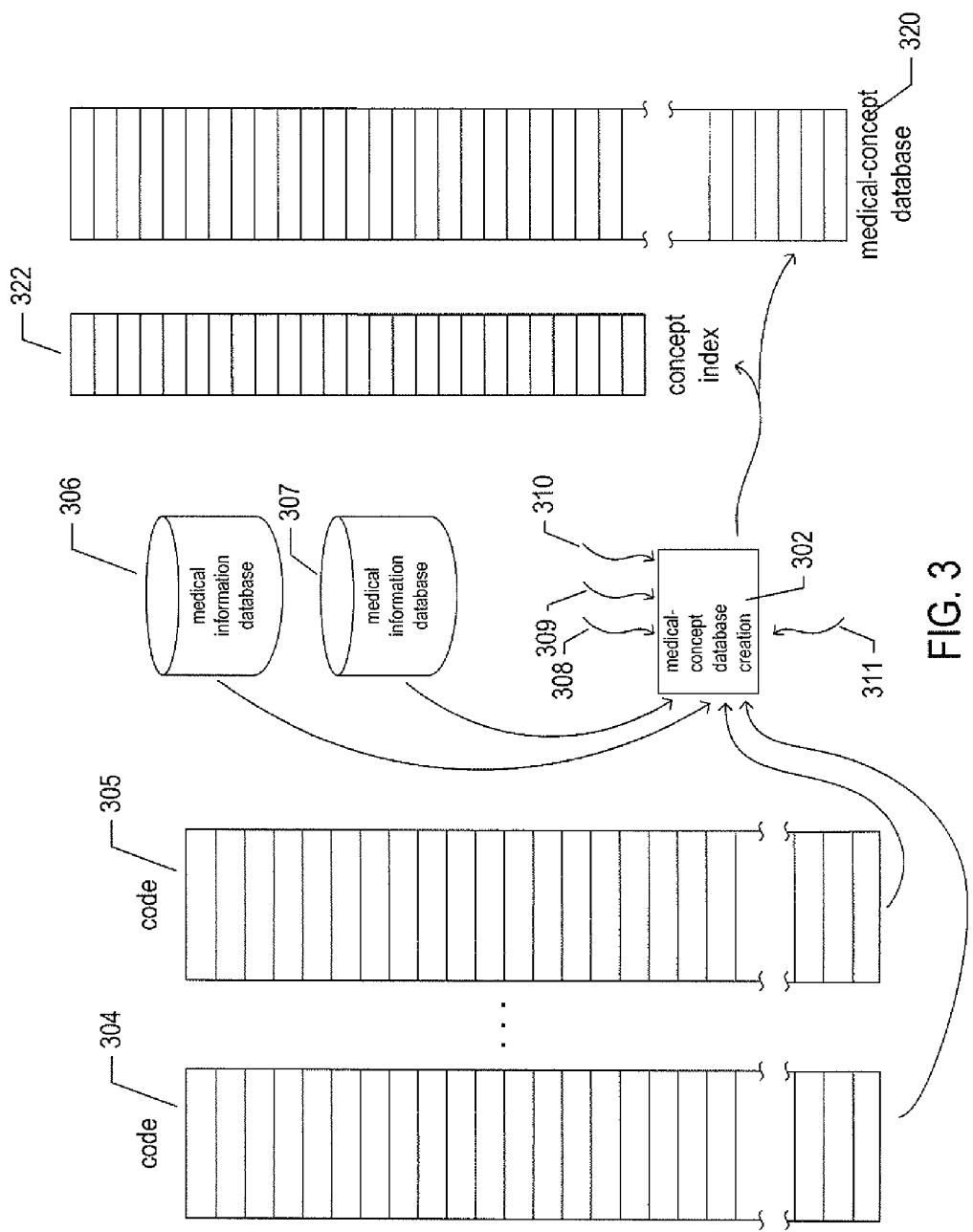
FIG. 3 illustrates preparation of a medical-concept database.

FIG. 3 illustrates preparation of a medical-concept database. Medical-concept-database creation 302 uses many different types of input information, including one, two, or more medical-concept codes 304-305, one or more medical-information databases 306-307, and potentially many other types of information inputs 308-311, including input from human analysts, processed medical records, journals and other medical literature, databases of EMRs and billing invoices, information gleaned from on-line sources, and many other types of information. From this information, a medical-concept database, represented by the column of entries 320 in FIG. 3, is prepared. Each entry may include a title or name for a particular medical concept, additional annotation information, references to various information sources, references to graphics or other explanatory material, and even a numeric identifier. In addition, the medical-concept database is generally associated with many different database indexes, such as medical-concept-database index 322, that allows medical concepts to be computationally efficiently identified based on key words, numerical data, and other search values. Any of many different types of databases, data-storage paradigms, and database management systems may be employed to create and manage the medical-concept database. For that reason, and because preparation of the medical-concept data is outside the scope of the current discussion, further description of preparation of the medical-concept database is not provided in this document. The medical-concept database may be stored within a computer system within which a medical-code translation system is implemented, one of multiple computer systems in which a distributed medical-codetranslation system is implemented, or may be stored and managed in a separate device accessible through electronic communications to one or more computer systems in which a medical-code translation system is implemented.

Figure 4:
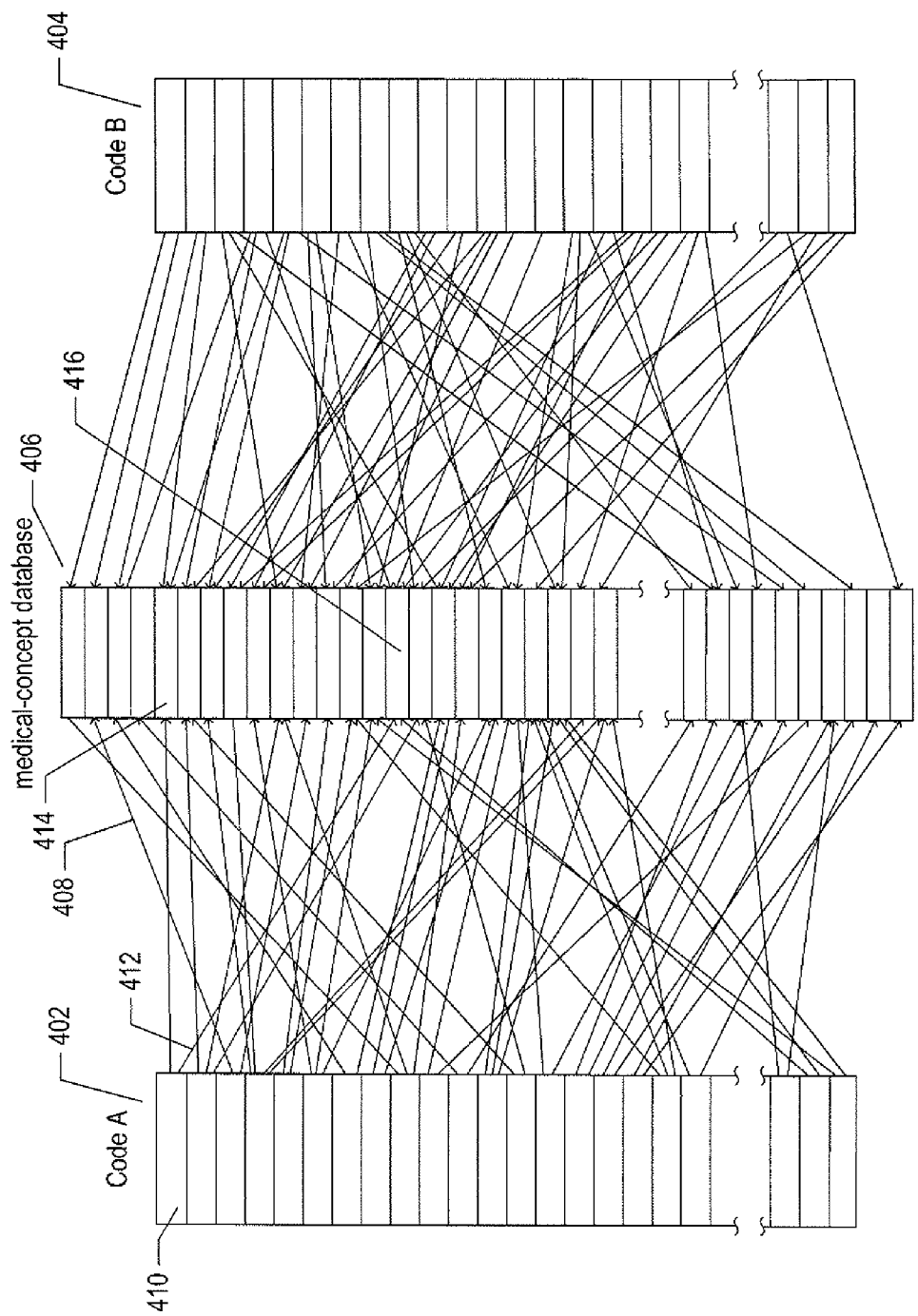
FIG. 4 illustrates associations between codewords and medical concepts stored in a medical-concept database.

In a next step, once the medical-concept database has been prepared, an exhaustive set of associations between codewords of medical-concept codes and medical concepts stored in the medical-concept database is prepared. FIG. 4 illustrates associations between codewords and medical concepts stored in a medical-concept database. In FIG. 4, a first column of entries 402 represents a first medical-concept code and a second column of entries 404 represents a second medical-concept code. The central column 406 represents a medical-concept database. A partial set of associations is represented by arrows, such as arrow 408, leading from entries in the medical-concept codes 402 and 404 to entries in the medical-concept database. These associations are one-to-many from codewords to medical concepts, as can easily be seen by considering the first entry 410 in the first medical-concept code 402, from which two arrows 408 and 412 emanate and point to two different medical concepts 414 and 416.

As one simple example, table 1, provided below, illustrates the medical concepts associated with each of the two example codeword entries shown in FIG. 2A:

| Codeword | Medical Concepts |
|---|---|
| 250.00 (ICD-9) | diabetes mellitus |
| Diabetes mellitus without mention of Complication, type II or unspecified type, not stated as uncontrolled | Diabetes Mellitus Type-II Diabetes Mellitus-controlled Diabetes Mellitus-without complications |
| E11.9 (ICD-10) Type 2 diabetes mellitus without complications | Diabetes Mellitus diabetes Mellitus Type-2 Diabetes Mellitus-without complications |

Figure 5:
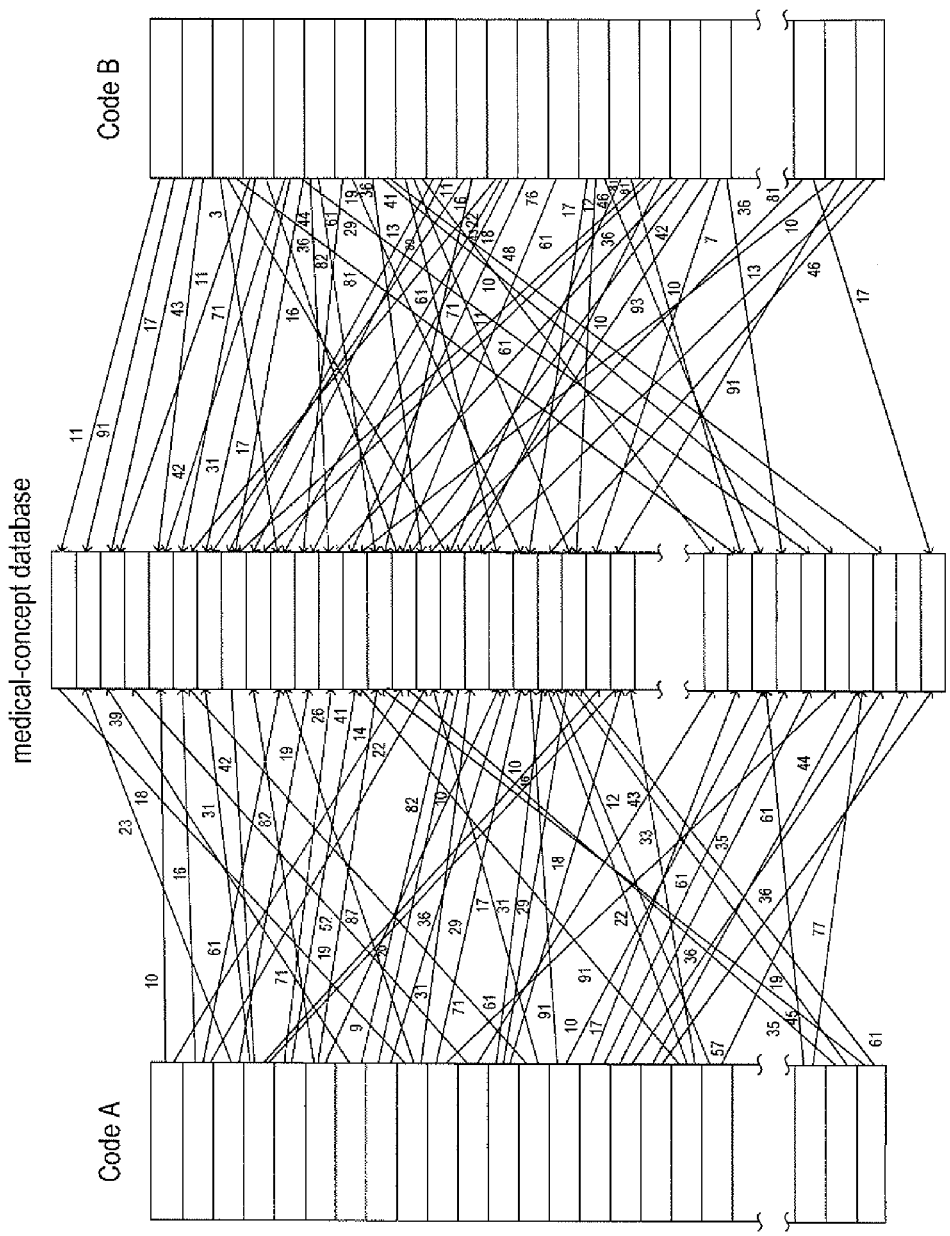
FIG. 5 illustrates numeric weights associated with each of the arrow-represented associations in FIG. 4.

In a third step, which, in some implementations, may be combined with the second step, weights are assigned to each of the associations between medical-concept-code entries, or codewords, and medical concepts stored within a medical-concept database. FIG. 5 illustrates numeric weights associated with each of the arrow-represented associations in FIG. 4. Many different types of weighting schemes, with different weighting values, can be used. For example, for simplicity, the weighting scheme used in FIG. 5 provides integer weights between 0 and 100 for each codeword/concept association. Other schemes may use real-valued weights between 0 and 1, as one example, or within some other range of real numbers. These weights may also be assigned by automated, semi-automated, manual, or a combination of automated, semi-automated, and manual methods. Considering, as a simple example, the two codewords listed in table 1, the weight assigned to the association of each codeword with the medical concept "diabetes mellitus" would most likely be relatively large and relatively significantly larger than the weight assigned to the association between codeword "250.00" and the medical concept "diabetes mellitus-controlled." Higher weights are given to concepts most informative in mapping particular codewords to a core set of medical concepts. The weightings may be partially determined based on statistical analyses, by various automated learning systems, but are often based at least partially on human analysis.

One, but by far not the only, approach to implementing method and system examples of the currently described methods and systems involves use of a relational database management system ("RDBMS"). Such systems can be managed and queried using the well-known SQL language, used below to illustrate certain portions of the example approach. In the example discussed below, rather than alpha-numeric values, the codewords are assumed to be integer values, for simplicity.

Figure 6:
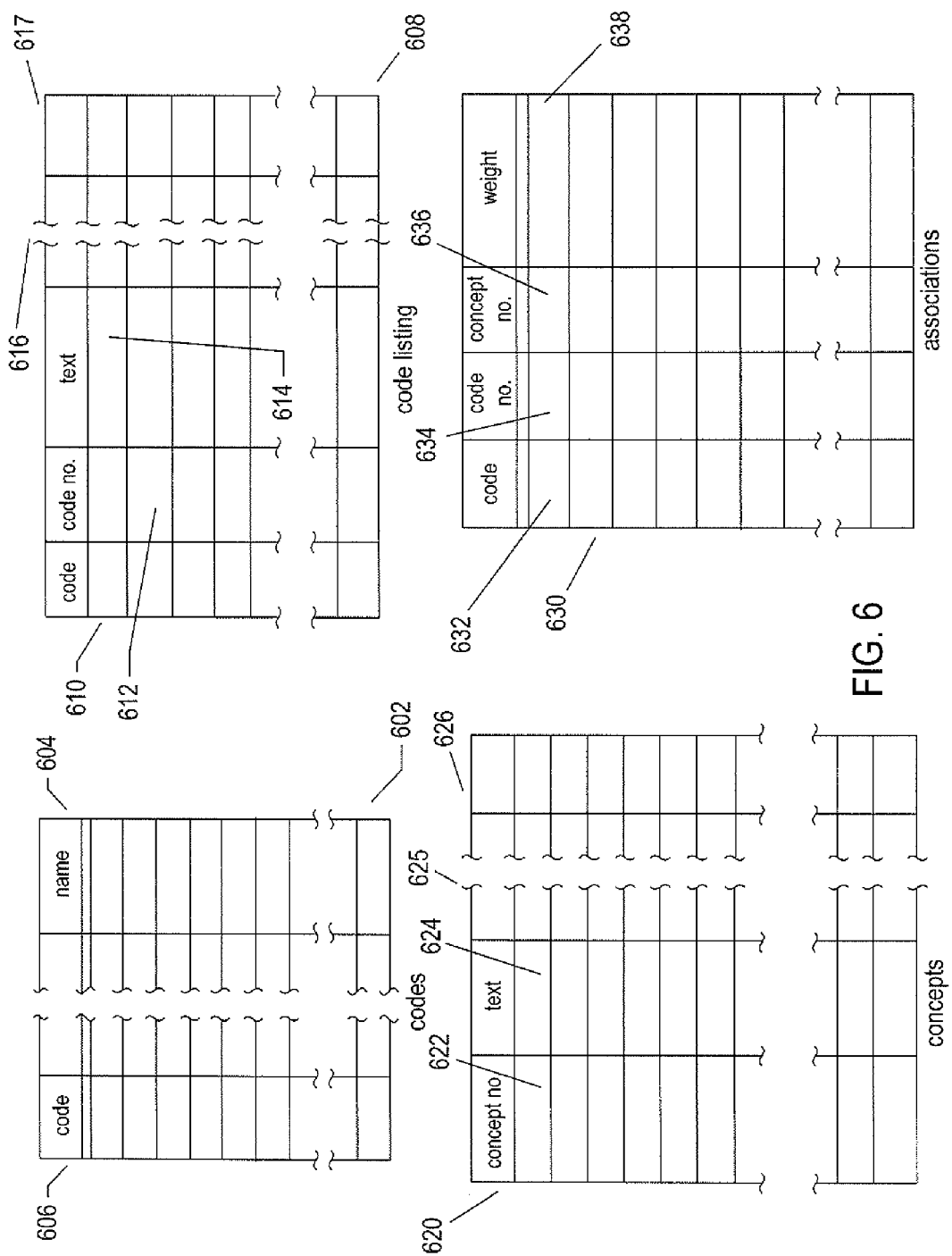
FIG. 6 illustrates four different RDBMS relational tables, referred to simply as "tables," that can be used to implement the types of information discussed above with reference to FIGS. 2A-5.

FIG. 6 illustrates four different RDBMS relational tables, referred to simply as "tables," that can be used to implement the types of information discussed above with reference to FIGS. 2A-5. A first table 602, named "codes," stores associations between the names of the various different medical-concept codes, stored in column 604 of table 602, and a unique numeric identifier for each medical-concept code, stored in column 606 of table 602. As one example, the medical-concept-code ICD-9 might be associated with a unique integer identifier "1," the medical-concept-code ICD-10 might be associated with the unique integer identifier "2," and other medical-concept codes may be associated with monotonically increasingly integers starting with "3." Of course, other numeric identifiers for the various medical-concept codes may be used, provided that each medical-concept code is associated with a unique numeric identifier.

The table "code listing" 608 stores the codewords, or entries, for the medical-concept codes listed in the table "codes" 602. Each entry in table 608 includes a unique identifier of a medical-concept code 610, the codeword within the medical-concept code 612, a textural annotation for the codeword 614, such as the text annotating the two codewords shown in FIG. 2A, and potentially many other types of information stored in additional columns 616-617.

The table "concepts" 620 contains the medical-concept database. Each medical concept is encoded within a row of the table. Each medical concept is encoded with a unique concept identifier 622, a textural representation of the concept 624, and potentially many additional types of information stored in column 625-626.

Finally, the table "associations" 630 stores the associations between codewords and medical-concept-database medical concepts, as illustrated in FIG. 5. Each row of the table represents a single association, represented in FIG. 5 by a directed arrow. Each association is encoded with a value for the medical-concept code in which the codeword resides 632, a numeric identifier for the codeword 634, a numeric identifier for the medical concept with which the codeword is associated 636, and a numeric weight value 638. Again, as with all tables used in the current example, many different types of data, many different ranges of values, and many different constellations of fields can be used to encode the information encoded within each of the example tables. The current example provides a simple, but informative and broadly illustrative, example of one approach to implementation of the currently described methods and systems.

Figure 7:
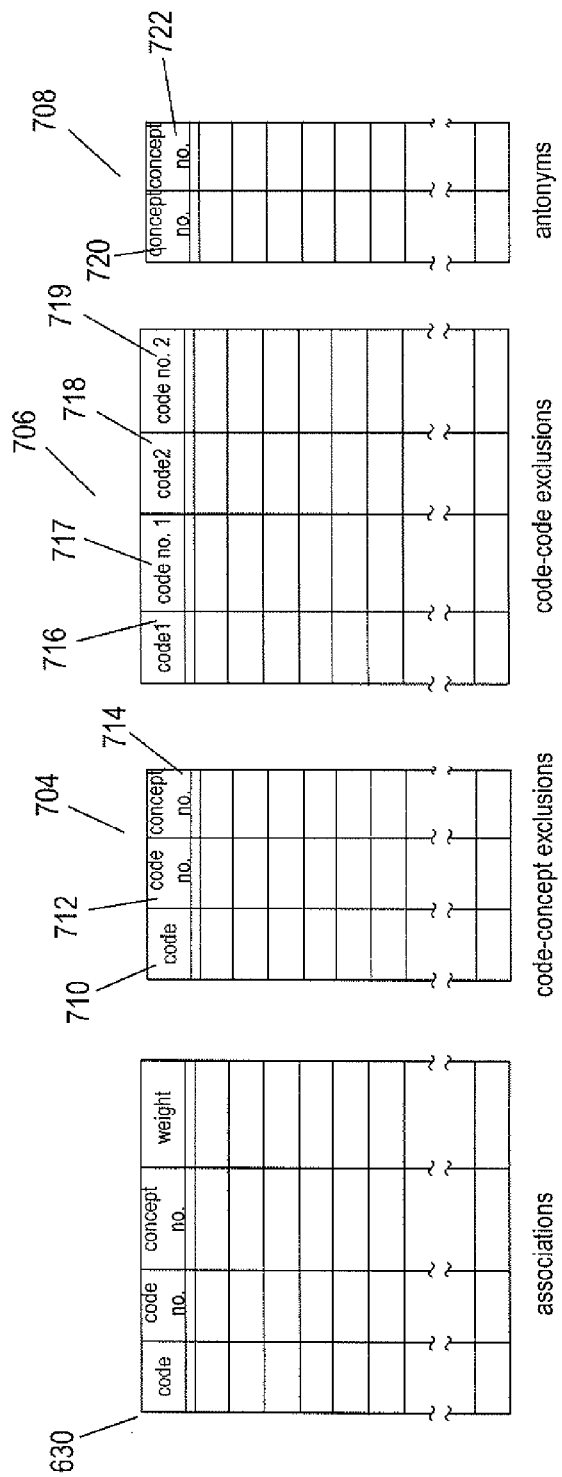
FIG. 7 illustrates three additional relational tables used, along with the relational tables illustrated in FIG. 6, in the described examples of a medical-concept-code-translation system and a medical-concept-code-translation method.

FIG. 7 illustrates three additional relational tables used, along with the relational tables illustrated in FIG. 6, in the described examples of a medical-concept-code-translation system and a medical-concept-code-translation method. FIG. 7 also shows the table "associations" 630 previously discussed with reference to FIG. 6. Below each table in FIG. 7, the SQL code for creating the table is provided, such as SQL code 702 that creates table 630. The three additional tables include the table "code-concept exclusions" 704, the table "code-code exclusions" 706, and the table "antonyms" 708.

The table "code-concept exclusions" lists pairs of codewords and concepts, each codeword represented by a pair of values in columns 710 and 712 and each concept represented by a value in column 714. Concept identifiers are obtained from the concept identifiers that uniquely identify medical concepts in column 622 of table 620 in FIG. 6 and the code and codeNo values in column 710 and 712 are taken from the values that uniquely identify each codeword in columns 610 and 612 of table 608 in FIG. 6. Information in this table prevents a codeword represented by the values in columns 710 and 712 in one row from being regarded as a synonym for, or match to, another codeword associated with the concept identified by the value in column 714 in the same row. The code/concept exclusions thus may filter candidate codeword translations to remove any candidate codeword translations associated with an excluded medical concept from the set of candidate translations for a particular source codeword.

The table "code-code exclusions" 706 provides listings of pairs of codewords that should not represent codeword translations. The first two columns 716 and 717 specify a first codeword of a first medical-concept code and columns 718-719 specify a second codeword of a second medical-concept code. This table essentially provides a specific first-codeword-to-second-codeword exclusion filter.

The third new table illustrated in FIG. 7, the table "antonyms" 708, lists pairs of medical concepts that are exclusive. A codeword associated with the first concept of a concept pair identified in column 720 of a particular row can never be translated to a second codeword that is associated with a concept identified in the second column 722 in the same row of the table "antonyms."

Figure 8:
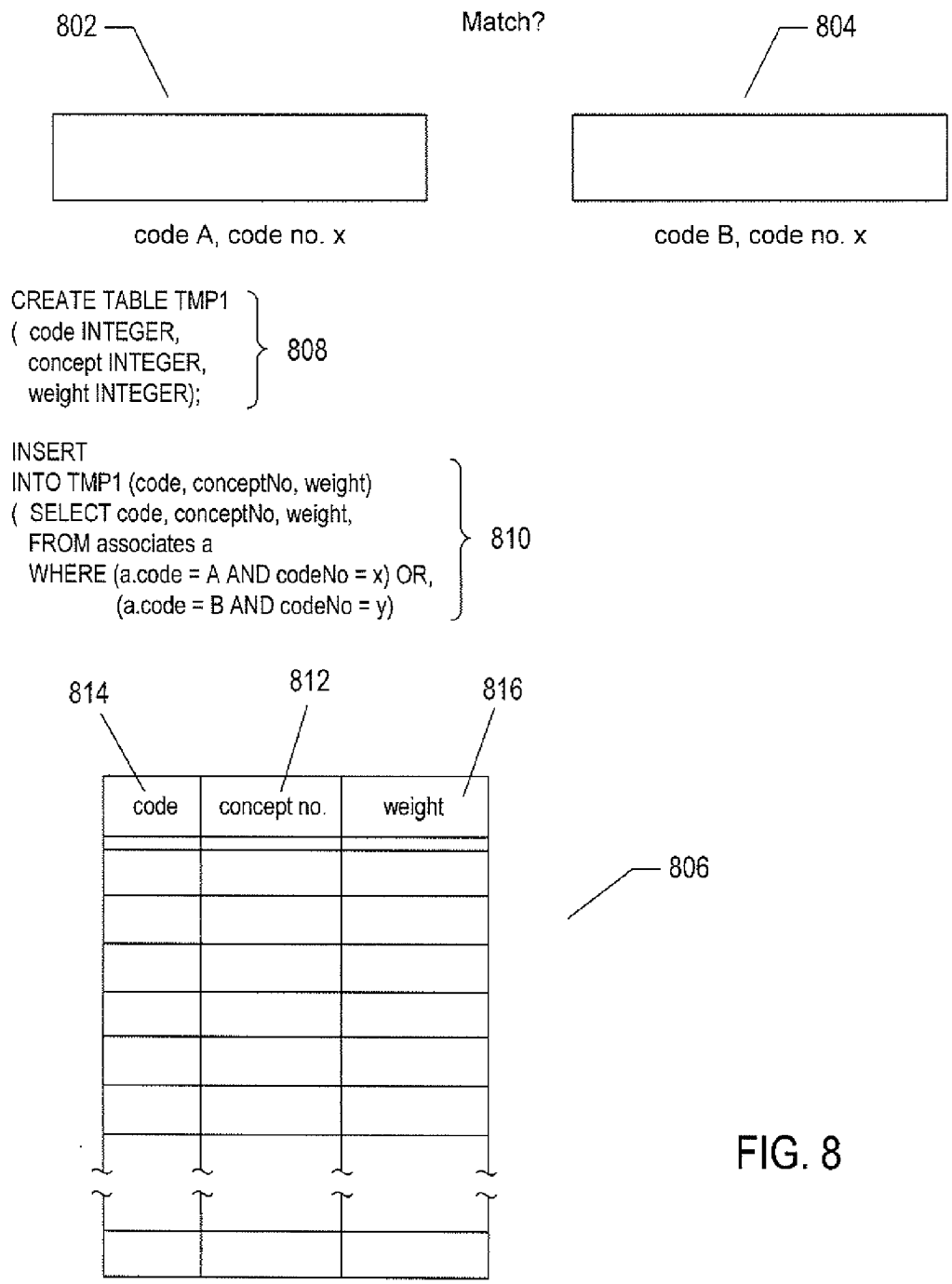
FIG. 8 illustrates a matching operation and an intermediate table used in generating a matching indication for a source codeword with respect to a candidate target codeword.

Using the above-described tables, and the information included in them, a codeword-translation process that represents an example of the methods to which the current application is directed is next described. FIG. 8 illustrates a matching operation and an intermediate table used in generating a matching indication for a source codeword with respect to a candidate target codeword. The process discussed with reference to FIG. 8 compares a first codeword 802, or source codeword, of a first medical-concept code, or source code, to a target codeword 804 of a second medical-concept code, or target code. In many cases, the target codeword may be a candidate target codeword that is being evaluated to determine whether or not the candidate target codeword should be promoted to a translation for the source codeword. The first medical-concept code is referred to as code "A." The source codeword 802 has the numeric value "x." The target codeword is selected from the second medical-concept code "B" and has the numeric value "y." The relational table "TMP1" 806 is used in the matching process and is created using the SQL statement 808 and populated with data using the SQL INSERT statement 810. This table includes the medical concepts, identified by the unique medical-concept identifier in column 812, associated either with the source codeword 802 or target codeword 804. The value in column 814 uniquely identifies either code "A" or code "B," thus implicitly identifying either source codeword 802 or target codeword 804. The value weight in column 816 is the weight of the association between either the source codeword or target codeword and the concept. As can be seen by the SQL INSERT statement, this table is populated with associations extracted from the table "associations" 730 in FIG. 7, where the extracted associations are related either to the source codeword 802 or target codeword 804.

Next, a number of numeric values are calculated from data stored in the intermediate tableTMP1 as well as certain of the other tables illustrated in FIG. 6 and 7. The value "totalNum" is the total number of distinct concepts in table TMP1, or the total number of distinct medical concepts associated with either or both of the source codeword and the target codeword, and can be computed using the following SQL statement:

totalNum=SELECT COUNT (conceptNo) from TMP1

The value "numLost" is the number of concepts associated with the source codeword that are not also associated with the target codeword, and is calculated by the following SQL statement:

numLost=SELECT COUNT (conceptNo) FROM TMP1 T1
   WHERE T1.code=A
     AND NOT EXISTS
     (SELECT *
     FROM TMP1 T2
     WHERE T2.code=B AND T2.conceptNo=T1.conceptNo)

The value "numAssumed" is the number of medical concepts associated with the target codeword 804 but not associated with the source codeword 802, and is calculated by the following SQL statement:

numAssumed=SELECT COUNT (conceptNo) FROM TMP1 T1
   WHERE T1.code=B
     AND NOT EXISTS
     (SELECT *
     FROM TMP1 T2
     WHERE T2.code=A AND T2.conceptNo=T1.conceptNo)

The value "numMatched" is the number of distinct concepts associated both with the source codeword and the target codeword, as computed by the following SQL statement:

numMatched=SELECT COUNT (conceptNo) FROM TMP1 T1
   WHERE T1.code=A
     AND EXISTS
     (SELECT *
     FROM TMP1 T2
     WHERE T2.code=B AND T1.conceptNo=T2.conceptNo)

The total weight of associations between the source codeword and medical concepts also associated with a target codeword is computed as the value "weightMatchedF" in the following SQL statement:

weightMatchedF=SELECT SUM (weight) FROM TMP1 T1
   WHERE T1.code=A
     AND EXISTS
     (SELECT *
     FROM TMP1 T2
     WHERE T2.code=B AND T1.conceptNo=T2.conceptNo)

The total weight of the associations from the target codeword to medical concepts also associated with the source codeword is computed as the value "weightMatchedR" by the following SQL statement:

weightMatchedR=SELECT SUM (WEIGHT) FROM TMP1 T1
   WHERE T1.code=B
     AND EXISTS
     (SELECT *
     FROM TMP1 T2
     WHERE T2.code=A AND T1.conceptNo=T2.conceptNo)

The total weight of all associations between the source codeword and associated medical concepts and the target codeword and associated medical concepts stored in the value "weightTotal," computed by the following SQL statement:

weightTotal=SELECT SUM (weight) FROM TMP1

The number of code/concept exclusions which are concepts associated with the target codeword that are listed as code-concept exclusions in the table "code-concepts exclusions" 714 in FIG. 7, and is calculated by the following SQL statement:

numCodeConceptExclusions=SELECT COUNT (conceptNo)
   FROM code-concept exclusions CE
      WHERE CE.code A
         AND EXISTS
           (SELECT *
           FROM associations a
           WHERE a.code=B AND
              a.codeNo=CE.conceptNo)

The number of code/code exclusions, which are potential exclusions that would prevent translation of source codeword 802 to target codeword 804, are computed by the following SQL statement:

numCodeCodeExclusions=SELECT COUNT (*) FROM code-code exclusions CC
   WHERE ((CC.code1=A AND CC.codeNo1=x AND
      CC.code2=B AND CC.codeNo2=y) OR
      (CC.code1=B AND CC.codeNo1=y AND
      CC.code2=A AND CC.codeNo2=x))

Finally, the number of concept pairs selected from the source codeword and target codeword that are listed as being antonyms in the table "Antonyms" 708 in FIG. 7 is computed by the following SQL statement:

```
numAntonymous = SELECT COUNT (*)
  FROM antonyms aa, associations a1, associations a2)
  WHERE (a1.code = A AND aa.conceptNo1 = a1.conceptNo AND
    EXISTS
      (SELECT * FROM associations a2
        WHERE a2.code = B AND aa.conceptNo2 = a2.conceptNo))
    OR (a1.code = A AND
      aa.conceptNo2 = a1.conceptNo AND
      EXISTS
        (SELECT * FROM associations a2
          WHERE a2.code = B AND
            aa.conceptNo1 = a2.conceptNo))
```

It should be noted that, in various other examples of the methods to which the current application is directed, fewer computed values can be computed and used in the matching operation. In yet alternative examples, a greater number of computed values are computed and used in the matching process. In yet additional examples, different computed values may be employed instead of in addition to, or in place of certain of the computed values discussed above.

In general, the matching operation may be considered to be a function of the above-computed values, returning a match value which indicates whether or not the source codeword and target codeword match or, in other cases, a numeric value that indicates the degree to which the target codeword matches the source codeword. In the former case, as one example, the match operation can be represented as the following function:

```
matchValue =   f (totalNum, numLost, numAssumed,
               numMatched, weightMatchedF, weightMatchedR,
               weightTotal, numCodeConceptExclusions,
               numCodeCodeExclusions, numAntonymous)
match =   {  1 when matchValue ≥ threshold
             0 when matchValue < threshold
```

A slightly different match operation is provided below, in pseudocode:

```
 1  bool match   (int totalNum, int numLost, int numAssumed,
                  int numMatched,
 2                int weightMatchedF, int weightMatchedR,
                  int weightTotal,
 3                int numCodeConceptExclusions,
                  int numCodeCodeExclusions,
 4                int numAntonymous, bool & exact, int & mValue)
 5  {
 6     if (numAntonymous > 0 || numCodeConceptExclusions >
                  0 ||
 7        numCodeCode Exclusions > 0) return false;
 8
 9     double v1, v2;
10     exact = numMatched = = totalNum;
11     v1 = numLost + numAssumed;
12     v2 = v1/totalNum;
13     if (v2 > THRESHOLD1) return false;
14     v1 = weightMatchedF + weightMatchedR;
15     v2 = v1/weightTotal;
16     if (v2<THRESHOLD2) return false;
17     v2 = v1/2;
18     if (v2 < THRESHOLD3) return false;
19     mValue = v2;
20     return true;
21  }
```

Figure 9A:
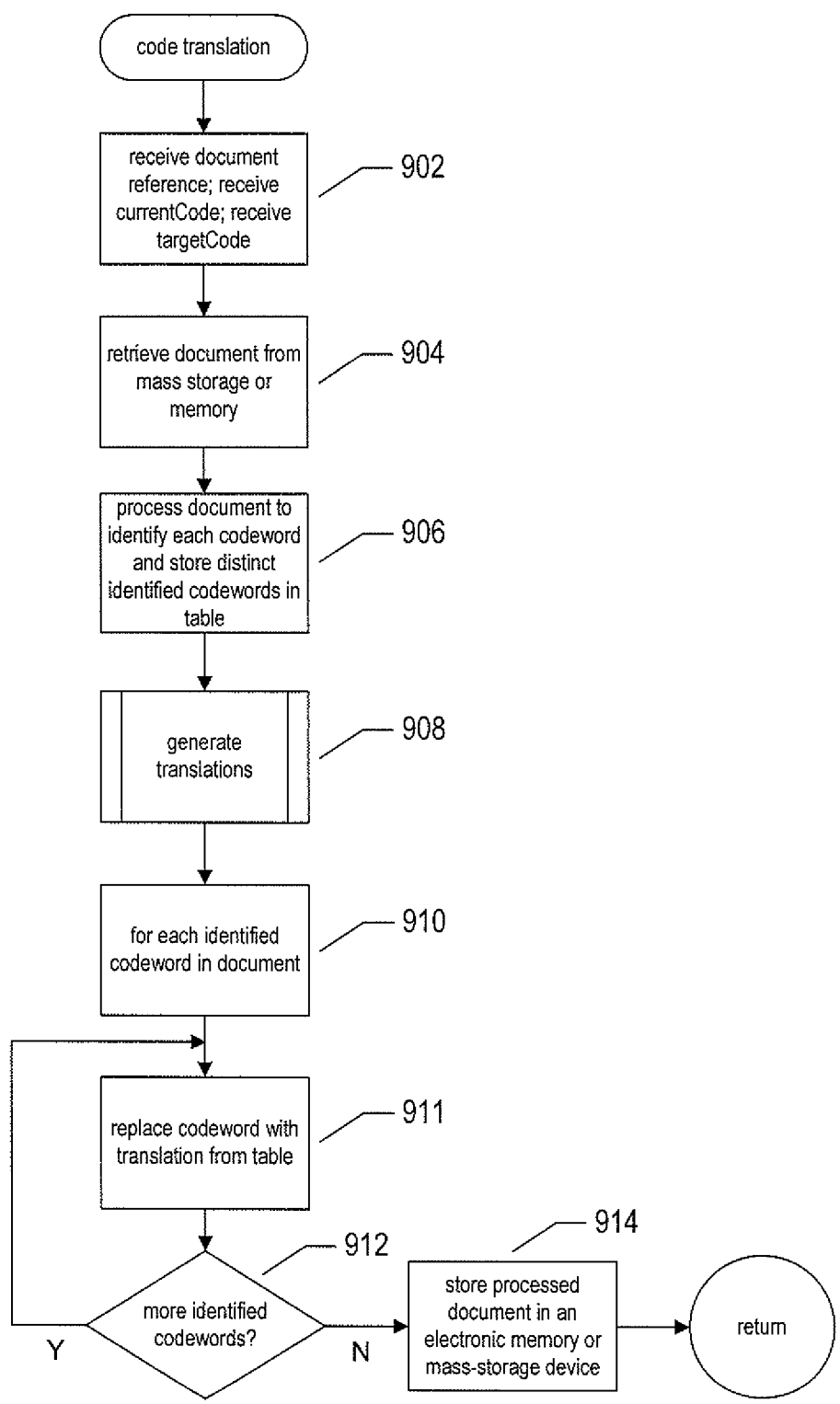
FIGS. 9A-B provide control-flow diagrams for a codeword-translation process that represents an example of the methods to which the current application is directed.
Figure 9B:
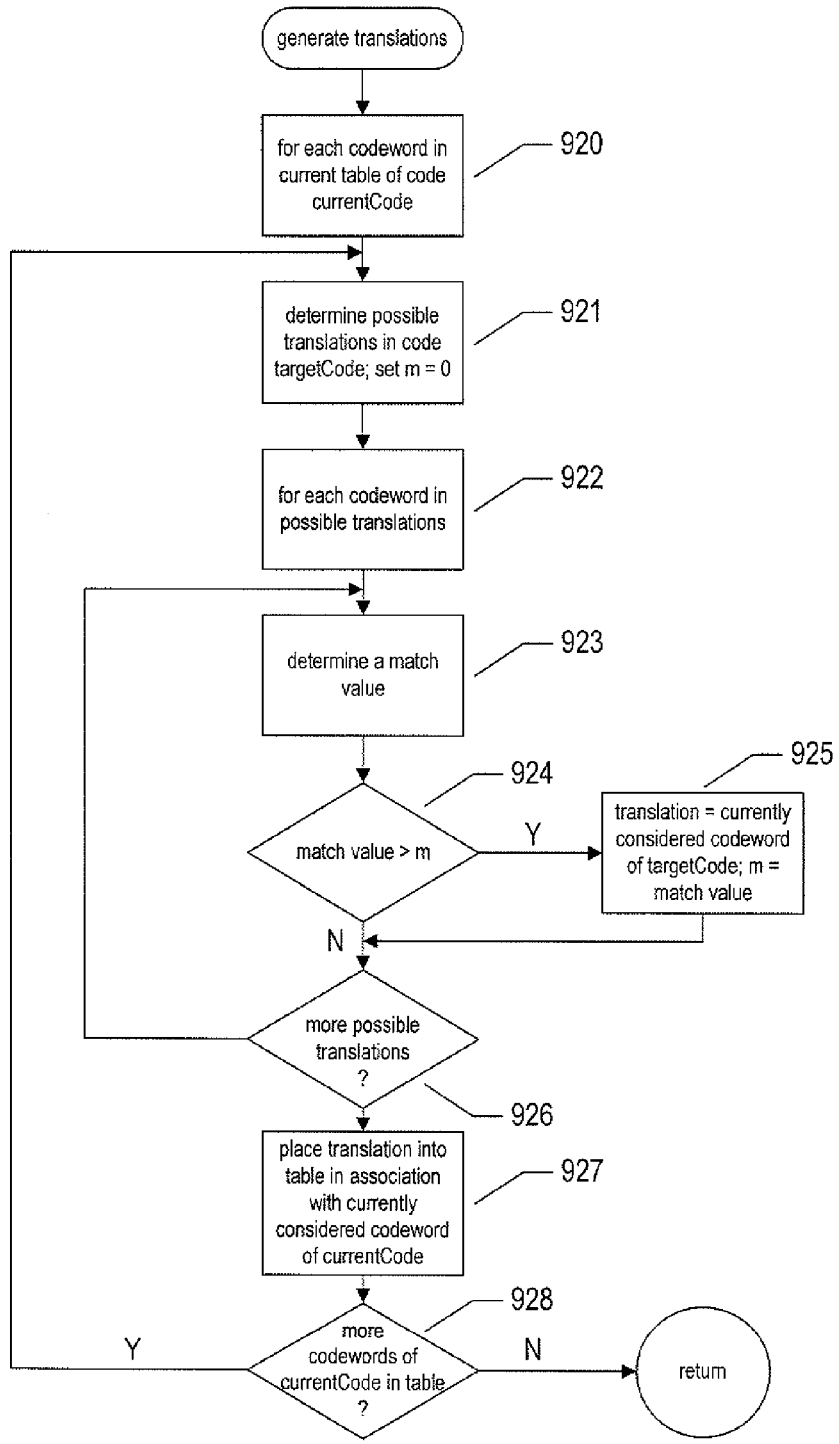

The function "match" returns a Boolean value in the variable parameter "exact" that indicates whether or not the match is exact as well as a numeric value in the variable parameter "mValue" that indicates a degree of matching. The remaining parameters are the calculated values discussed above. First, on lines 6-7, if any code/code exclusions, code/concept exclusions, or antonymous concept exclusions have been discovered, then the routine "match" returns false. Otherwise, on line 10, the variable parameter "exact" is set to indicate whether the value "numMatched" is equal to the value "totalNum," indicating that all concepts associated either with the source codeword or target codeword are associated with both the source codeword and target codeword. Next, on lines 11-12, the local variable v2 is set to the sum of numLost and numAssumed divided by totalNum. If the ratio of lost and assumed concepts to the total number of concepts is greater than a threshold value "THRESHOLD1," the routine "match" returns false. Note that the routine "match" may return the Boolean value false even for a source codeword and target codeword that exactly match, but this rare case can be detected by inspecting the value returned in the variable parameter "exact." In general, the routine "match" returns false when too many concepts associated either with the source codeword or target codeword are not commonly associated with the source codeword and target codeword. Next, on lines 14-15, the routine "match" computes the relative weight of common associations of the source codeword and target codeword with respect to the total weight of associations of the source codeword and target codeword. When this computed value falls below a threshold value THRESHOLD2, the routine "match" returns false. Thus, the routine "match" returns false when the relative weight of common associations with respect to the total weight of associations falls below some threshold value considered to be a minimal weight of common associations needed to match the source codeword to the target codeword. A third threshold, THRESHOLD3, a threshold for the total weight of common associations, is applied, on line 18, so that when the total weight of the common associations falls below THRESHOLD3, the routine "match" returns false. Otherwise, the summed weights of common associations is returned in the variable parameter "mValue" and the routine "match" returns the Boolean value true, on lines 19-20. Again, many alternative implementations of the matching operation are possible, FIGS. 9A-B provide control-flow diagrams for a codeword-translation process that represents an example of the methods to which the current application is directed. The method uses the above-described routine "match." Beginning with FIG. 9A, in step 902, the codeword-translation process receives a document or a reference to a document containing codewords of a first medical-concept code as well as references to the first medical-concept code, currentCode, and a second medical-concept code, targetCode, into which instances of codewords in the document are to be translated. In step 904, the codeword-translation process retrieves the referenced document from a mass-storage device from memory. In step 906, the codeword-translation process electronically processes the document to identify each medical codeword within the reference document and stores the distinct identified codewords in a table, along with references to the locations of their occurrences in the referenced document. Next, in step 908, the codeword-translation process calls the routine "generateTranslations" to generate target codewords for each of the source codewords stored in the table in step 906. Finally, in the for-loop of steps 910-912, the codeword-translation process replaces each original source codeword in the reference document with corresponding codeword translations from the table and stores the processed document containing translated codewords in an electronic memory or mass-storage device in step 914.

Continuing to FIG. 9B, FIG. 9B provides a control-diagram for the routine "generateTranslations" called in step 908 of FIG. 9A. In the outer for-loop of steps 920-928, each codeword of currentCode stored in the table 906 in FIG. 9A is considered. In step 921, possible translations for the currently considered source codeword are determined, the possible translations for the currently considered source codeword obtained, as one example, using the SQL statement:

SELECT a2.codeNo FROM associations a1, a2
  WHERE a1.code=A AND a1.codeNo=x AND
    a2.code=B AND a1.conceptNo=a2.conceptNo In the for-loop of steps 922-926, the above-described routine "match" is called for the currently considered source codeword and each of the possible translations, with any candidate translation for which the routine "match" returns a match value greater than the largest match value so far determined temporarily stored, in step 925, as the so-far-detected best candidate for translation. Upon completion of the inner for-loop of steps 922-926, the best translation identified in the inner for-loop is stored in the table in association with the currently considered source codeword. When there are more source codewords to consider, as determined in step 928, control flows back to step 921. Otherwise, the routine "generateTranslations" returns. Note that it is assumed, in this implementation, that at least one acceptable translation will be found. When this assumption is incorrect, an additional local variable may be set, in step 921, with an indication that no translation was found. That indication will be entered in the table in association with the currently considered source codeword when no translation is found in the target medical-concept code.

Not only can source codewords of one medical-concept code be translated to target codewords of another medical-concept code, the information discussed above can be used for many other medical-code-related tasks. For example, it is straightforward to generate a list of all underlying medical concepts associated with a particular codeword by, as one example, using the concisely coded SQL statement:

SELECT CL.text FROM code listing CL, associations a
WHERE a.conceptNo=z AND a.code=CL.code AND
  a.codeNo=CL.codeNo AND a.weight>THRESHOLD This is but one of many different possible examples of medical-concept-code related tasks that can be carried out using the stored information and techniques that represent examples of the methods and systems to which the current application is directed.

Although the present invention has been described in terms of particular embodiments, it is not intended that the invention be limited to these embodiments. Modifications within the spirit of the invention will be apparent to those skilled in the art. For example, medical-code-translation systems and methods can be implemented by varying any of many different design and implementation parameters, including selection of hardware platforms, operating systems, programming languages, control structures, data structures, modular organizations, and other such implementation parameters. As discussed above, while relational databases are used to provide example implementations, any of many different types of data-storage systems may be used instead of relational data systems. While, in the above example, numerous different numeric values are calculated for the source and target codewords in the match operation, in alternative examples, other numeric values may be computed and used to compute a degree of similarity or another metric returned by the match operation.

It is appreciated that the previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

The invention claimed is:

1. A medical-code translation system comprising:
  a computer system that includes a processor, one or more electronic memories, and one or more mass-storage devices;
  a medical-concept database stored within, or accessible to, the computer system;
  and computer instructions that control operation of the medical-code-translation system, encoded in one or more of the one or more electronic memories and one or more mass-storage devices to
    receive and store, in memory, a source codeword from a source medical code,
    identify candidate target codewords of a target medical-concept code, using indications of medical concepts stored in the medical-concept database, that are associated with at least one medical concept with which the source code is associated,
    remove, from the candidate target codewords, excluded codewords to generate a set of remaining candidate target codewords; and
    select a target codeword corresponding to the source codeword that, when compared to the source codeword in a matching operation, generates a comparison metric that indicates a degree of matching with the source code greater than the degree of matching indicated by the comparison metrics generated for each of the other remaining candidate target codewords in matching operations.

2. The medical-code translation system of claim 1 wherein the medical-code translation system maintains digitally-encoded weighted associations between codewords of the source medical code and medical concepts stored in the medical-concept database and digitally-encoded weighted associations between codewords of the target medical code and medical concepts stored in the medical-concept database, the digitally-encoded weighted associations stored in one or more of the one or more electronic memories, one or more mass-storage devices, and medical-concept database.

3. The medical-code translation system of claim 2 wherein the medical-code translation system maintains digitally encoded exclusions stored in one or more of the one or more electronic memories, one or more mass-storage devices, and medical-concept database:
   code/concept exclusions;
   code/code exclusions; and
   concept/concept exclusions.

4. The medical-code translation system of claim 3 wherein the medical-code-translation system removes, from the candidate target codewords, excluded codewords to generate a set of remaining candidate target codewords by:
   removing candidate target codewords associated with a medical concept that is excluded from association with the source codeword by a code/concept exclusion;
   removing candidate target codewords excluded from association with the source codeword by a code/code exclusion; and
   removing candidate target codewords associated with a medical concept that is excluded from association with a medical concept associated with the source codeword by a concept/concept exclusion.

5. The medical-code translation system of claim 2 wherein the matching operation compares a source codeword with a target codeword by:
   computing one or more values;
   comparing each of the one or more values with a corresponding threshold value to generate a comparison value; and
   returning one or more indications of matching based on the one or more computed values and one or more comparison values.

6. The medical-code translation system of claim 5 wherein the computed values include one or more of:
   a number of medical concepts associated with the source codeword;
   a number of medical concepts associated with the target codeword;
   a number of medical concepts associated with either or both of the source codeword and the target codeword;
   a number of medical concepts associated with the source codeword that are not also associated with the target codeword;
   a number of medical concepts associated with the target codeword that are not also associated with the source codeword;
   a sum of the weights of association of the medical concepts associated with the source codeword that are also associated with the target codeword;
   a sum of the weights of association of the medical concepts associated with the target codeword that are also associated with the source codeword; and
   a sum of the weights of association of the medical concepts associated with the source codeword that are not also associated with the target codeword
a sum of the weights of association of the medical concepts associated with the target codeword that are not also associated with the source codeword.

7. The medical-code translation system of claim 5 wherein the comparison values include one or more of:
   a value indicating whether or not a sum of the number of medical concepts associated with the source codeword that are not also associated with the target codeword and the number of medical concepts associated with the target codeword that are not also associated with the source codeword divided by the number of medical concepts associated with either or both of the source codeword and the target codeword is greater than a first threshold value;
   a value indicating whether or not a sum of the sum of the weights of association of the medical concepts associated with the source codeword that are also associated with the target codeword and the sum of the weights of association of the medical concepts associated with the target codeword that are also associated with the source codeword divided by the a sum of the weights of association of the medical concepts associated with the source codeword and the weights of association of the medical concepts associated with the target codeword is greater than a second threshold value; and
   a value indicating whether or not the not a sum of the sum of the weights of association of the medical concepts associated with the source codeword that are also associated with the target codeword and the sum of the weights of association of the medical concepts associated with the target codeword that are also associated with the source codeword divided by 2 is greater than a third threshold value.

8. The medical-code translation system of claim 5 wherein the one or more indications of matching include one or more of:
   a Boolean value indicating whether or not the source codeword matches the target codeword; and
   a numeric value indicating a degree of matching between the source codeword and the target codeword.

9. Computer instructions encoded in an electronic memory, mass-storage device, optical disk, or other physical data-storage medium that, when executed in a computer system that includes a processor, one or more electronic memories, one or more mass-storage devices, and a medical-concept database stored within, or accessible to, the computer system, implement a control program that controls operation of a medical-code-translation system that:
   receives and stores, in memory, a source codeword from a source medical code,
   identifies candidate target codewords of a target medical-concept code, using the medical-concept database, that are associated with at least one medical concept with which the source code is associated,
   removes, from the candidate target codewords, excluded codewords to generate a set of remaining candidate target codewords; and
   selects a target codeword corresponding to the source codeword that, when compared to the source codeword in a matching operation, generates a comparison metric that indicates a degree of matching with the source code greater than the degree of matching indicated by the comparison metrics generated by each of the other remaining candidate target codewords.

10. The computer instructions of claim 9 wherein the medical-code translation system maintains weighted associations between codewords of the source medical code and medical concepts stored in the medical-concept database and weighted associations between codewords of the target medical code and medical concepts stored in the medical-concept database.

11. The computer instructions of claim of 10 wherein the medical-code translation system maintains encoded exclusions, including:
   code/concept exclusions;
   code/code exclusions; and
   concept/concept exclusions.

12. The computer instructions of claim 11 wherein the medical-code-translation system removes, from the candidate target codewords, excluded codewords to generate a set of remaining candidate target codewords by:
   removing candidate target codewords associated with a medical concept that is excluded from association with the source codeword by a code/concept exclusion;
   removing candidate target codewords excluded from association with the source codeword by a code/code exclusion; and
   removing candidate target codewords associated with a medical concept that is excluded from association with a medical concept associated with the source codeword by a concept/concept exclusion.

13. The computer instructions of claim 10 wherein the matching operation compares a source codeword with a target codeword by:
   computing one or more values;
   comparing each of the one or more values with a corresponding threshold value to generate a comparison value; and
   returning one or more indications of matching based on the one or more computed values and one or more comparison values.

14. The computer instructions of claim 13 wherein the computed values include one or more of:
   a number of medical concepts associated with the source codeword;
   a number of medical concepts associated with the target codeword;
   a number of medical concepts associated with either or both of the source codeword and the target codeword;
   a number of medical concepts associated with the source codeword that are not also associated with the target codeword;
   a number of medical concepts associated with the target codeword that are not also associated with the source codeword;
   a sum of the weights of association of the medical concepts associated with the source codeword that are also associated with the target codeword;
   a sum of the weights of association of the medical concepts associated with the target codeword that are also associated with the source codeword; and
   a sum of the weights of association of the medical concepts associated with the source codeword and the weights of association of the medical concepts associated with the target codeword.

15. The computer instructions of claim 13 wherein the comparison values include one or more of:
   a value indicating whether or not a sum of the number of medical concepts associated with the source codeword that are not also associated with the target codeword and the number of medical concepts associated with the target codeword that are not also associated with the source codeword divided by the number of medical concepts associated with either or both of the source codeword and the target codeword is greater than a first threshold value;
   a value indicating whether or not a sum of the sum of the weights of association of the medical concepts associated with the source codeword that are also associated with the target codeword and the sum of the weights of association of the medical concepts associated with the target codeword that are also associated with the source codeword divided by the a sum of the weights of association of the medical concepts associated with the source codeword and the weights of association of the medical concepts associated with the target codeword is greater than a second threshold value; and
   a value indicating whether or not the not a sum of the sum of the weights of association of the medical concepts associated with the source codeword that are also associated with the target codeword and the sum of the weights of association of the medical concepts associated with the target codeword that are also associated with the source codeword divided by 2 is greater than a third threshold value.

16. The computer instructions of claim 13 wherein the one or more indications of matching include one or more of:
   a Boolean value indicating whether or not the source codeword matches the target codeword; and
   a numeric value indicating a degree of matching between the source codeword and the target codeword.

17. A method carried out within a computer system that includes a processor, one or more electronic memories, one or more mass-storage devices, and a medical-concept database stored within, or accessible to, the computer system, the method comprising:
   receiving and storing, in memory, a source codeword from a source medical code,
   identifying candidate target codewords of a target medical-concept code, using indications of medical concepts stored in the medical-concept database, that are associated with at least one medical concept with which the source code is associated,
   removing, from the candidate target codewords, excluded codewords to generate a set of remaining candidate target codewords; and
   selecting a target codeword corresponding to the source codeword that, when compared to the source codeword in a matching operation, generates a comparison metric that indicates a degree of matching with the source code greater than the degree of matching indicated by the comparison metrics generated for each of the other remaining candidate target codewords in matching operations.

18. The method of claim 17 further including maintaining weighted associations between codewords of the source medical code and medical concepts stored in the medical-concept database and weighted associations between codewords of the target medical code and medical concepts stored in the medical-concept database.

19. The method of claim computer 18 further including maintaining encoded exclusions, including:
   code/concept exclusions;
   code/code exclusions; and
   concept/concept exclusions.

20. The method of claim 19 wherein removing, from the candidate target codewords, excluded codewords to generate a set of remaining candidate target codewords further includes:

removing candidate target codewords associated with a medical concept that is excluded from association with the source codeword by a code/concept exclusion;

removing candidate target codewords excluded from association with the source codeword by a code/code exclusion; and removing candidate target codewords associated with a medical concept that is excluded from association with a medical concept associated with the source codeword by a concept/concept exclusion.

21. The method of claim 18 wherein the matching operation compares a source codeword with a target codeword by:

computing one or more values;

comparing each of the one or more values with a corresponding threshold value to generate a comparison value; and returning one or more indications of matching based on the one or more computed values and one or more comparison values.

22. The method of claim 21 wherein the computed values include one or more of:

a number of medical concepts associated with the source codeword;

a number of medical concepts associated with the target codeword;

a number of medical concepts associated with either or both of the source codeword and the target codeword;

a number of medical concepts associated with the source codeword that are not also associated with the target codeword;

a number of medical concepts associated with the target codeword that are not also associated with the source codeword;

a sum of the weights of association of the medical concepts associated with the source codeword that are also associated with the target codeword;

a sum of the weights of association of the medical concepts associated with the target codeword that are also associated with the source codeword; and a sum of the weights of association of the medical concepts associated with the source codeword and the weights of association of the medical concepts associated with the target codeword.

23. The method of claim 21 wherein the comparison values include one or more of:

a value indicating whether or not a sum of the number of medical concepts associated with the source codeword that are not also associated with the target codeword and the number of medical concepts associated with the target codeword that are not also associated with the source codeword divided by the number of medical concepts associated with either or both of the source codeword and the target codeword is greater than a first threshold value;

a value indicating whether or not a sum of the sum of the weights of association of the medical concepts associated with the source codeword that are also associated with the target codeword and the sum of the weights of association of the medical concepts associated with the target codeword that are also associated with the source codeword divided by the a sum of the weights of association of the medical concepts associated with the source codeword and the weights of association of the medical concepts associated with the target codeword is greater than a second threshold value; and a value indicating whether or not the not a sum of the sum of the weights of association of the medical concepts associated with the source codeword that are also associated with the target codeword and the sum of the weights of association of the medical concepts associated with the target codeword that are also associated with the source codeword divided by 2 is greater than a third threshold value.

24. The method of claim 21 wherein the one or more indications of matching include one or more of:

a Boolean value indicating whether or not the source codeword matches the target codeword; and a numeric value indicating a degree of matching between the source codeword and the target codeword.

* * * * *